(12) United States Patent
Buchholz et al.

(10) Patent No.: US 6,538,021 B1
(45) Date of Patent: Mar. 25, 2003

(54) METHOD FOR PRODUCING LUTEOLIN AND LUTEOLIN DERIVATIVES

(75) Inventors: Herwig Buchholz, Frankfurt (DE); Ralf Rosskopf, Munster (DE); Alice Lichtenberg, Darmstadt (DE); Christine Kraus, Schwarzheide (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/830,284

(22) PCT Filed: Oct. 13, 1999

(86) PCT No.: PCT/EP99/07687

§ 371 (c)(1),
(2), (4) Date: Apr. 25, 2001

(87) PCT Pub. No.: WO00/26206

PCT Pub. Date: May 11, 2000

(30) Foreign Application Priority Data

Oct. 30, 1998 (DE) .......................................... 198 50 283
Nov. 2, 1998 (DE) .......................................... 198 50 572

(51) Int. Cl.$^7$ ..................... A61K 31/352; C07D 311/22
(52) U.S. Cl. ....................................... 514/456; 549/403
(58) Field of Search ........................... 549/403; 514/456

(56) References Cited

FOREIGN PATENT DOCUMENTS

| DE | 19544905 | 6/1997 |
|----|----------|--------|
| EP | 633022 | 1/1995 |
| EP | 807 435 | 11/1997 |
| FR | 2578422 | 9/1986 |
| FR | 2687572 | 8/1993 |
| FR | 2699818 | 7/1994 |
| WO | 95/21018 | 8/1995 |

OTHER PUBLICATIONS

Hydroxy Isoflavones as Antioxidants for Edible Oils, Stanley Z. Dziedzic & Bertran J.F. Hudson, Food Chemistry 11 (1983) pp. 161–166.

R. Mosquera et. al.: "Synthesis of O–(beta–hydroxyethyl) derivatives of Diosmetin." Indian Journal of Chemistry, Section B, Bd. 35B, No. 1, Jan., 1996 (1996–01), pp. 19–22, XP000872742.

G. Kitkei et. al.: "Cyclodehydrogenation of 2'-Hydroxy-chalcones with Hypervalent Iodine Reagent. A New Synthesis of Flavones." Liebigs Annalen Der Chemie, Bd. 1995, pp. 1711–1715, XP002130763.

*Primary Examiner*—Ba K. Trinh
(74) *Attorney, Agent, or Firm*—Millen, White, Zelano & Branigan, P.C.

(57) ABSTRACT

Disclosed is a method for producing compounds of formula (I), wherein $R^1$ represents H or $(CH_2)_m OH$, $R^2$ represents H or $(CH_2)_n OH$, $R^3$ represents H or $(CH_2)_p OH$ and m, n and p represent 2–8 independently from one another. Said compounds are particularly suitable for use as food supplements. They are highly suitable for use in cosmetic formulations as UV filters, for instance.

14 Claims, No Drawings

METHOD FOR PRODUCING LUTEOLIN AND LUTEOLIN DERIVATIVES

The invention relates to a process for the preparation of compounds of the formula I

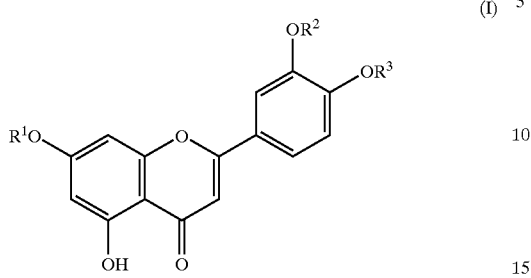
(I)

in which $R^1$ is H or $(CH_2)_m OH$, $R^2$ is H or $(CH_2)_n OH$, $R^3$ is H or $(CH_2)_p OH$, and m, n and p in each case, independently of one another are 2 to 8.

The compound of the formula I in which $R^1$, $R^2$ and $R^3$ are H is luteolin. For the purposes of the present invention, he compounds of the formula I in which at least one of the radicals $R^1$, $R^2$ or $R^3$ has a meaning other than H are referred to as luteolin derivatives.

Luteolin has various advantageous properties. Luteolin is an excellent antioxidant and a very good free-radical scavenger. In addition, it inhibits both enzymatic, nonenzymatic and $CCl_4$-induced lipid peroxldations. Luteolin has a favorable influence on the card ovascular system and can prevent the development of arteriosclerosis. The anticancer effect of luteolin is evident inter alia from the considerable antiproliferative activity against various human tumor cell lines. Anti-inflammatory, antiviral, antibacterial and radioprotective properties of luteolin have also been reported. As an inhibitor of the enzyme aldose reductase, luteolin can also have a preventative effect against the development of diabetic cataracts.

The luteolin derivatives of the formula I have similarly advantageous properties to luteolin itself.

Known processes for the preparation of compounds of the formula I have the disadvantage that they involve, for example, two or more synthesis stages and/or produce unsatisfactory yields of product. For example, it has hitherto only been possible to isolate luteolin from plants or to prepare it by multistage syntheses. The synthesis from suitable chalcones and hesperidin is possible only with unsatisfactory yields [U. Achterrath-Tuckermann et al., Planta Med. 39 (1980) 38; D. Nagarathnam et al., J. Org. Chem. 56 (1991) 4884; Y.-H. Lu et al., Yao Hsueh Hsueh Pao 15 (1980) 477; G. Litkei et al., Liebigs Ann. 9 (1995) 1711; Y. Xing et al., Zhongguo Yiyao Gongye Zazhi 25 (1994) 484].

The object was therefore to develop a process for the preparation of the compounds of the formula I which avoids or at least reduces the disadvantages of known processes, in particular permits a single-stage preparation of the compounds of the formula I from readily available precursors and/or permits the preparation of the compounds of the formula I in relatively high yield.

Surprisingly, we have found that this object is achieved if the process for the preparation of the compounds of the formula I

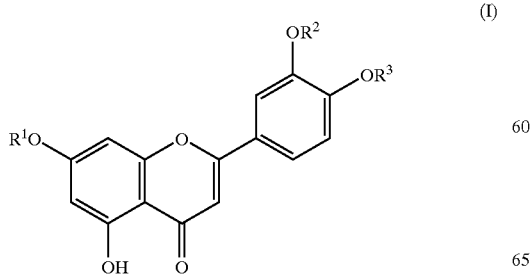
(I)

in which $R^1$ is H or $(CH_2)mOH$, $R^2$ is H or $(CH_2)nOH$, $R^3$ is H or $(CH_2)_pOH$, and m, n and p in each case, independently of one another, are 2 to 8, is carried out such that compounds of the formula II

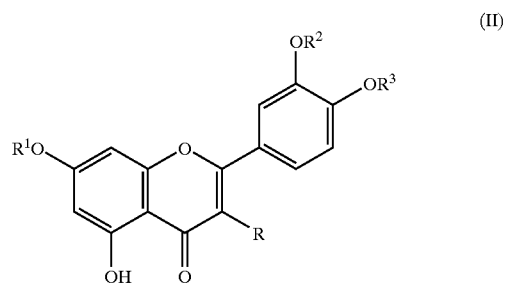
(II)

in which $R^1$, $R^2$ and $R^3$ in each case, independently of one another, have the meanings given in formula I, and R is

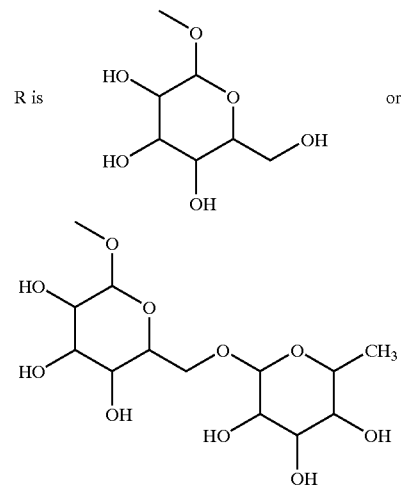

are reduced with sodium dithinite $Na_2S_2O_4$ in an aqueous alkaline medium.

The invention thus provides a process for the preparation of compounds of the formula I

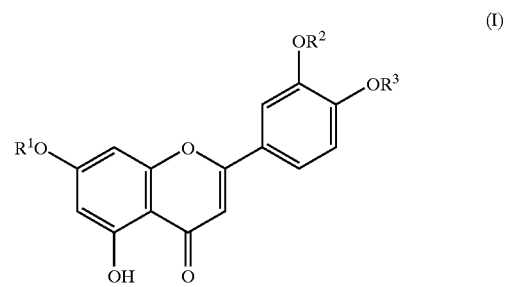
(I)

in which $R^1$ is H or $(CH_2)_m OH$, $R^2$ is H or $(CH_2)_n OH$, $R^3$ is H or $(CH_2)_p OH$, and m, n and p are in each case, independently of one another, 2 to 8, characterized in that compounds of the formula II

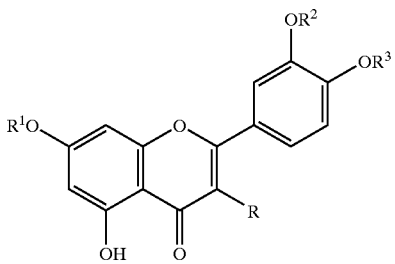

(II)

in which $R^1$, $R^2$ and $R^3$ in each case, independently of one another, have the meanings given in formula I, and

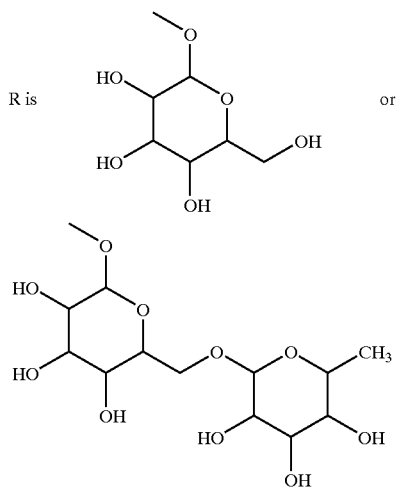

are reduced with sodium dithionite $Na_2S_2O_4$ in an aqueous alkaline medium.

The process according to the invention is notable in particular for the fact that the preparation of the compounds of the formula I takes place in a simple manner and/or in higher yields than was possible by processes known hitherto.

The present invention also provides foodstuffs which have been enriched with one or more compounds of the formula I, and also the use of the compounds of the formula I as food supplements.

The foodstuffs which can be enriched according to the present invention with one or more compounds of the formula I include all materials suitable for consumption by animals or for consumption by humans, for example vitamins and provitamins thereof, fats, minerals or amino acids. Foodstuffs which can be enriched according to the present invention with one or more compounds of the formula I are, for example, also foodstuffs originating from a single natural source, for example sugar, unsweetened juice, nectar or puree of a single plant species, for example unsweetened apple juice (e.g. including a mixture of different types of apple juice), grapefruit juice, orange juice, stewed apples, apricot nectar, tomato juice, tomato sauce, tomato puree, etc. Further examples of foodstuffs which can be enriched according to the present invention with one or more compounds of the formula I are corn or grain of a single plant species and materials prepared from such plant species, for example grain syrup, rye flour, wheatmeal or oat bran. Mixtures of such foodstuffs are also suitable for being enriched according to the present invention by one or more compounds of the formula I, for example multivitamin preparations, mineral substance mixtures or sugared juice. Further examples of foodstuffs which can be enriched according to the present invention with one or more compounds of the formula I which may be mentioned are foodstuff preparations, for example prepared cereals, bakery products, mixed drinks, foodstuffs prepared specifically for children, such as yoghurt, diet foodstuffs, low-calorie foodstuffs or animal feed.

The foodstuffs which can be enriched according to the present invention with one or more compounds of the formula I thus include all palatable combinations of carbohydrates, lipids, proteins, inorganic elements, trace elements vitamins, water and active metabolites of slants and animals.

The foodstuffs which can be enriched according to the present invention with one or more compounds of the formula I, and the food supplements which contain one or more compounds of the formula : are preferably used orally, e.g. in the form of foods, pills, tablets, capsules, powders, syrups, solutions or suspensions.

The foodstuffs according to the Invention enriched with one or more compounds of the formula I can be prepared using techniques which are well known to the person skilled In the art.

Furthermore, the invention provides cosmetic or pharmaceutical formulations which comprise one or more compounds of the formula I, and the use of one or more compounds of the formula I in cosmetic or pharmaceutical formulations. The cosmetic formulations which comprise one or more compounds of the formula I, and the use of one or more compounds of the formula I in cosmetic formulations is preferred.

Whilst about 30 years ago sunlight was regarded as therapeutic and safe because of the synthesis of vitamin D, in recent years, opinion in this connection has changed considerably, not only from a medical viewpoint. The potential dangers associated both with natural and artificial irradiation with sunlight has been pushed into the foreground of awareness. In particular, a change in behavior has been brought about as a result of knowledge about the effect of sunlight on skin aging and the development of skin cancer.

As is known, the skin is sensitive to solar rays, which may cause ordinary sunburn or an erythema, but also burns of greater or lesser severity.

Solar rays too, however, also have other negative effects: they cause the skin to lose its elasticity and form wrinkles and thus lead to premature aging. In some cases, dermatoses can also be observed, and in extreme cases, skin cancer can result.

It is also desirable to protect hair against photochemical damage in order to prevent changes in shades, bleaching or damage of a mechanical nature.

As is known, the most harmful part of solar rays is formed from the ultraviolet rays having a wavelength of less than 400 nm. It is also known that, as a result of the presence of the ozone layer in the earth's atmosphere, which absorbs some solar radiation, the lower limit of the ultraviolet rays which reach the earth's surface is about 280 nm.

The main aim in the field of sun protection is therefore actually to ensure good protection against UVB and UVA radiation.

The compounds of the formula I can be present in the cosmetic or pharmaceutical preparation alone or, of course, also in combination with further light protection filters from different classes of substance, alone or in combination. Light protection filters of other classes of substance are, for example, organic or inorganic UV and UVB filters, IR filters or VIS filters. Particular preference is given to the combination with organic UV filters or mixtures thereof.

The invention therefore also provides the use of one or more compounds of the formula I in cosmetic formulations such as sunscreens, skin creams or skin gels, hair gels or cosmetic sticks, in particular as UV filters.

Further suitable organic UV filters are all UVA and UVB filters known to the person skilled in the art. For both UV regions there are a large number of tried and tested substances known from the specialist literature, e.g. benzylidenecamphor derivatives, such as 3-(4'-methylbenzylidene)-dl-camphor (e.g. Eusolex® 6300)

3-benzylidenecamphor (e.g. Mexoryl® SD), polymers of N-{(2 and 4)-[(2-oxoborn-3-ylidene)-methyl]benzyl}acrylamide (e.g. Mexoryl® SW), N,N,N-trimethyl-4-(2-oxoborn-3-ylidenemethyl)-anilinium methylsulfate (e.g. Mexoryl® SK) or α- (2-oxoborn-3-ylidene)toluene-4-sulfonic acid (e.g. Mexoryl® SL), benzoyl- or dibenzoylmethanes, such as 1-(4-tert-butylphenyl)-3-(4-methoxyphenyl)propane-1,3-dione (e.g. Eusolex® 9020) or 4-isopropyldibenzoylmethane (e.g. Eusolex® 8020), benzophenones, such as 2-hydroxy-4-mrethoxybenzophenone (e.g. Eusolex® 4360) or 2-hydroxy-4-methoxybenzophenone-5-sulfonic acid and its sodium salt (e.g. Uvinul® MS-40), methoxycinnamic esters, such as octyl methoxycinnamate (e.g. Eusolex® 2292), isopertyl 4-methoxycinnamate, e.g. as a mixture of the isomers (e.g. Neo Heliopan® E 1000), salicylate derivatives, such as 2-ethylhexyl salicylate (e.g. Eusolex® OS), 4-isopropylbenzyl salicylate (e.g. Megasol®) or 3,3,5-trimethylcyclohexyl salicylate (e.g. Eusolex® HMS), 4-aminobenzoic acid and derivatives, such as 4-aminobenzoic acid, 2-ethylhexyl 4-(dimethylamino)benzoate (e.g. Eusolex® 6007), ethoxylated ethyl 4-aminobenzoate (e.g. Uvinul ® P25), and further substances, such as 2-ethylhexyl 2-cyano-3,3-diphenylacrylate (e.g. Eusolex® OCR), 2-phenylbenzimidazole-5-sulfonic acid, and its potassium, sodium and triethanolamine salts (e.g. Eusolex® 232), 3,3'-(1,4-phenylenedimethylene)-bis(7,7-dimethyl-2-oxobicyclo[2.2.1]hept-1-ylmethanesulfonic acid, and its salts (e.g. Mexoryl® SX) and 2,4,6-trianilino-(p-carbo-2'-ethylhexyl-1'-oxy)-1,3,5-triazine (e.g. Uvinul® T 150).

These organic UV filters are usually incorporated into cosmetic formulations in an amount of from 0.5 to 10% by weight, preferably 1–8%.

Examples of further suitable organic UV filters are 2-(2H-benzotriazol-2-yl)-4-methyl-6-(2-methyl-3-(1,3,3,3-tetramethyl-1-(trimethylsilyloxy)-disiloxanyl)propyl)phenol (e.g. Silatrizole®), 4,4'-[(6-[4-((1,1-dimethylethyl)aminocarbonyl)-phenylaminol-1,3,5-triazne-2,4-diyl)diimino]bis-(2-ethylhexyl benzoate) (e.g. Uvasorb® HEB), α-(trimethylsilyl)-ω-[triethylsilyl)oxy]poly(oxy-(dimethyl [and about 6% methyl[2-[p-[2,2-bis-(ethoxycarbonyl]vinyl]phenoxy]-1-methyleneethyl] and about 1.5% methyl[3-[p-[2,2-bis(ethoxy-carbonyl)vinyl)phenoxy)propenyl) and 0.1 to 0.4% (methylhydrogen]silylene]] (n≈60) (e.g. Parsol® SLX), 2,2'-methylenebis(6-(2H-benzotriazol-2yl)-4-(1,1,3,3-tetramethylbutyl)phenol) (e.g. Tinosorb® M), 2,2'-(1,4-phenylene)bis(1H-berzimidazole-4,6-disulfonic acid, monosodium salt) (e.g. Neo Heliopan® AP) and 2,4-bis{[4-(2-ethylhexyloxy)-2-hydroxy]phenyl}-6-(4-methoxyphenyl)-1,3,5-triazine (e.g. Tinosorb® S).

These organic UV filters are usually incorporated into cosmetic formulations in an amount of from 0.5 to 20 percent by weight, preferably 1–15%.

Possible inorganic UV filters are those From the group of titanium dioxides, such as coated titanium dioxide (e.g. Eusolex® T-2000), zinc oxides (e.g. Sachtotec®), iron oxide or also cerium oxide. These inorganic UV filters are usually incorporated into cosmetic formulations in an amount of from 0.5 to 20 percent by weight, preferably 2–10%.

In the formulations in which compounds of the formula I are present together with other UV filters, the compounds of the formula I act, for example, as antioxidants and free-radical scavengers. In addition, wash such Formulations, broadband UV protection is achieved. The invention thus also provides the use of one or more compounds of the formula I in cosmetic or pharmaceutical formulations as UV filter, antioxidant and/or free-radical scavenger.

The invention further provides a method of protecting the skin and/or natural or sensitized hair from solar rays, where a cosmetic preparation comprising one or more compounds of the formula I as light protection filter is applied to the skin or the hair.

If desired, the sunscreens according to the invention may also comprise one or more chemical substances having self-tanning properties.

Chemical substances having self-tanning properties which may be used are all natural and synthetic substances known to the person skilled in the art which are suitable for the preparation of cosmetic formulations. These may either be vegetable extracts or synthetic self-tanning agents, such as dihydroxyacetone or α-ketols.

Furthermore, the formulations according to the invention may also be used for the preventative treatment of inflammations and allergies of the skin and also, in certain cases, for preventing certain types of cancer.

The preparation according to the invention is used as an agent for protecting the human epidermis or hair, or also sensitized hair or as a sunscreen.

"Sensitized hair" is understood as meaning hair which has been subjected to a permanent waving treatment, or to a coloring or bleaching process.

The cosmetic preparation according to the invention is used for protecting the human epidermis against solar radiation. For this purpose, it is in a variety of forms customarily used for this type of product. Thus, it may in particular be in the form of a lotion or emulsion, such as a cream or milk (O/W, W/O), in the form of oily-alcoholic, oily-aqueous or aqueous-alcoholic gels or as solid sticks, or can be formulated as an aerosol.

The formulation can comprise cosmetic adjuvants which are customarily used in this type of preparation, such as thickeners, emollients, moisturizers, interface-active agents, emulsifiers, preservatives, antifoams, perfumes, waxes, lanolin, propellants, dyes and/or pigments which color the composition itself or the skin, and other ingredients customarily used in cosmetics.

The dispersant or solubilizer may be an oil, wax or other fatty substances, a lower monoalcohol or a lower polyol or mixtures thereof. Particularly preferred monoalcohols or polyols include ethanol, isopropanol, propylene glycol, glycerol and sorbitol.

A preferred embodiment of the invention is an emulsion in the form of a protective cream or milk and which, apart from the compound(s) of the formula I as UV filter—and, where appropriate, also further light protection filters—comprises fatty alcohols, fatty acids, fatty acid esters, in particular triglycerides of fatty acids, lanolin, natural or synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycol, such as propylene glycol, and/or a polyol, such as glycerol, and oils, waxes and fatty acid esters, such as triglycerides of fatty acids.

The cosmetic preparation according to the invention can also be in the form of an alcoholic gel which comprises one or more lower alcohols or lower polyols, such as ethanol, propylene glycol or glycerol, and a thickener, such as silica. The oily-alcoholic gels fur,her comprise natural or synthetic oil or wax.

The solid sticks consist of natural or synthetic waxes and oils, fatty alcohols, fatty acids, fatty acid esters, lanolin and other fatty substances.

If a preparation is formulated as an aerosol, use is usually made of the customary propellants, such as alkanes, fluoroalkanes and chlorofluoroalkanes.

If the intention is for the composition according to the invention to protect natural or sensitized hair from solar irradiation, it may be in the form of a shampoo, lotion, gel or emulsion for rinsing out, in which case the respective formulation is applied before or after shampooing, before or after coloring or bleaching, or before or after permanent waving; or the composition is in the form of a lotion Or gel for styling and treating, a lotion or gel for brushing or blow waving, a hairspray, permanent waving composition, colorant or bleach for the hair. As well as comprising the compound(s) of the formula I as organic UV filter(s)—and, where appropriate, further light protection filters—this composition may comprise various adjuvants used in this type of composition, such as interface-active agents, thickeners, polymers, emollients, preservatives, foam stabilizers, electrolytes, organic solvents, silicone derivatives, oils, waxes, antigrease agents, dyes and/or pigments which color the composition itself or the hair, or other ingredients customarily used for haircare.

The cosmetic preparations according to the invention can be prepared using techniques which are well known to the person skilled in the art.

Of the compounds of the formula I, preference is given to the compound in which $R^1$, $R^2$ and $R^3$ are H, and the compounds in which $R^1$ is $(CH_2)_m OH$, $R^2$ is $(CH_2)_n OH$ and $R^3$ is $(CH_2)_p OH$ and m, n and p in each case, independently of one another are 2 to 8. These compounds of the formula I are also referred to above and below as compounds of the formula I*

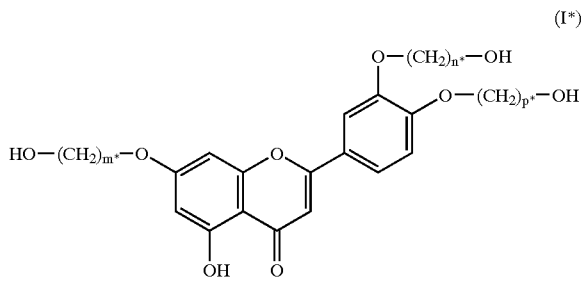

(I*)

in which m*, n* and p* in each case, independently of one another, are 2 to 8. Particular preference is given to the compounds of the formula I*.

The present invention also relates to these compounds of the formula I*.

In the compounds of the formula I or I*, m, n and p or m*, n* and p* in each case, independently of one another, are 2, 3, 4, 5, 6, 7 or 8. Preferably, m, n and p or m* n* and p* in each case, independently of one another, are 2, 3 or 4. Particularly preferably, m, n and p or m*, n* and p* are identical, and very particularly preferably m, n and p or m*, n* and p* are 2.

The compounds of the formula I* have better solubility in water than luteolin itself. Surprisingly, it has also been found that the compounds of the formula I* are colorless. Foodstuffs according to the invention which have been enriched with one or more compounds of the formula I, and cosmetic formulations according to the invention which comprise one or more compounds of the formula I* are particularly preferred. Accordingly, the use of one or more compounds of the formula I* as food supplements and the use thereof in cosmetic formulations, e.g. as UV filters, is also particularly preferred.

The present invention provides an advantageous process for the preparation of the compounds of the formula I by reduction of the compounds of the formula II. Here, either rutin or its derivatives alone, isoquercetin or its derivatives alone or also mixtures thereof, such as a mixture of rutin and isoquercetin, or a mixture of rutin derivatives and isoquercetin derivatives, can be used as starting materials in the reaction.

According to the process of the invention, the compounds of the formula II are dissolved or suspended in water, preferably in boiling water, and, after an alkaline pH has been established, e.g. using alkali metal or alkaline earth metal hydroxides or carbonates, such as sodium hydroxide solution or sodium carbonate, sodium dithionite $Na_2S_2O_4$ is added. The reaction mixture is then stirred until the reaction is complete, preferably under reflux.

The compounds of the formula II are available commercially or can be isolated or prepared by methods which are well known to the person skilled in the art and are described in the literature (e.g. in standard works such as Houben-Weyl, Methoden der organischen Chemie [Methods of organic chemistry], Georg-Thieme-Veriag, Stuttgart).

Suitable reaction temperatures for the process according to the invention are temperatures between 25 and 100° C. The process according to the invention is preferably carried out at reaction temperatures of from 50 to 100° C., in particular at reaction temperatures of from 80 to 100° C.

A suitable pH for the process according to the invention is a pH between 7.5 and 11. The process according to the invention is preferably carried out at a pH of From 8 to 9, in particular at a pH from 8.2 to 8.7.

Suitable bases for the process according to he invention are, for example, alkali metal or alkaline earth metal hydroxides, hydrogen carbonates or carbonates. Preferred bases are chosen from NaOH, KOH, NaHCO$_3$, KHCO$_3$, Na$_2$CO$_3$, K$_2$CO$_3$. Particular preference is given to carrying out the process according to the invention using bases chosen from NaOH and Na$_2$CO$_3$.

Suitable weight ratios of the compound of the formula II: water for the process according to the invention are ratios of from 1:10 to 1:200. The process according to the invention is preferably carried out with weight ratios of the compound of the formula II: water of from 1:50 to 1:150, in particular with weight ratios of from 1:80 to 1:120.

Suitable weight ratios of the compound of the formula II: sodium dithionite Na$_2$S$_2$O$_4$ for the process according to the invention are ratios of from 1:1 to 1:100. Preference is given to carrying out the process according to the invention with weight ratios of the compound of the formula II : sodium dithionite Na$_2$S$_2$O$_4$ from 1:5 to 1:40, in Darticular with weight ratios of from 1:8 to 1:25.

The process according to the invention is preferably carried out under atmospheric pressure.

The progress or the end of the reaction, and also the analysis of the reaction product can be carried out, for example, using HPLC, e.g. usina standard HPLC instruments and columns comprising reversed phase materials with C$_{18}$-alkyl coating.

Alternatively, the progress and the end of the reaction can also be monitored using thin layer chromatography (TLC).

When the reaction is complete, the reaction product is isolated by customary methods. For the purposes of the present invention, "customary work-up" means the following:

the reaction mixture is cooled, for example to a temperature of 5° C. and then neutralized by adding an acid, for example hydrochloric acid. The reaction mixture is preferably stirred further following the addition of the acid, for example for 1 to 12 h at a temperature of 0 or 5° C. The crude product which crystallizes out during this time is separated off from the remaining reaction mixture, for example by mechanical methods such as suction filtration or filtration. The purity of the crude product is usually >96%.

For further work-up, it may, for example, be admixed with demineralized water, stirred under reflux for a period of time and then filtered while hot, e.g. at a temperature of 85° C. The purity of the resulting product is usually >99%. However, even purities >99.5% can be achieved directly.

The solid is then dried, e.g. for 12 h at a pressure of 200 mbar and a temperature of 50° C.

Even without Further details, it is assumed that a person skilled in the art can utilize the above description in the widest sense. The preferred embodiments are therefore merely to be regarded as a descriptive disclosure which is in no way limiting.

The complete disclosure of all of the applications and publications listed above and below are incorporated into this application by reference.

The examples below serve to illustrate the present invention. However, they are in no way to be regarded as limiting.

EXAMPLES

The sources of supply for the substances used are as follows:
 Rutin: Merck KGaA, Article No. 500017
 Trihydroxyethylrutin: Merck KGaA, Article No. 501902
The reaction was monitored and the reaction products were analyzed using HPLC.

HPLC Conditions Using Standard HPLC Equipment:
 Column: LiChrosorb® RP18 (reversed phase—material with C$_{18}$-alkyl coating and a particle size of 5 μm (Merck KGaA, Article No. 151355)),
 Mobile phase: Mixture of acetonitrile and water in a volume ratio of 20:80 (pH 2.6)
 Flow rate: 1 ml/min,
 Wavelength: 260 nm,
 Temperature: 30° C.,
 Sample volume: 10 μl,
 Sample preparation: Dissolve 5 mg of the sample in 3 ml of methanol and make up to 10 ml with the mobile phase,
 Retention times: Rutin: 7.3 min, Luteolin: 46.4 min, Trihydroxyethylrutin: 10.6 min, Trihydroxyethylluteolin: 43.3 min.

Example 1

Preparation of Luteolin 60 g of rutin are suspended in 6 l of demineralized wazer and, at 100° C., firstly 210 ml of 32% strength aqueous sodium hydroxide solution and then 600 g of sodium dithionite are added thereto. The mixture is then refluxed for a further 12 h with stirring, and the suspension is cooled to 5° C., slowly neutralized with 195 ml of fuming hydrochloric acid and stirred for 1 h at 0° C. Customary work-up gives 23.3 g of crude luteolin with a purity of 96.5%. Further purification and drying produces 20.9 g of luteolin with a purity of 99.6%.

Example 2

Preparation of tri(hydroxyethyl)luteolin 5 g of tri(hydroxyethyl)rutin are dissolved in 500 ml of demineralized water and, at 100° C., firstly 42.5 g of sodium carbonate and then 100 g of sodium dithionite are added thereto. The mixture is refluxed for a further hour with stirring, is then cooled to room temperature and stirred for a further 72 h. 65 ml of fuming hydrochloric acid are then added at 5° C. and the mixture is stirred for a further 12 h. Customary work-up produces 1.95 g of tri(hydroxyethyl) luteolin with a purity of 98%.

Example 3

Preparation of Luteolin 3.5 g of isoquercetin are carefully suspended in 500 ml of demineralized water at 60° C., and 8.8 ml of 32% strength aqueous sodium hydroxide solution are introduced into the resulting yellow suspension. During this addition, a dark-red colored clear solution forms. 25 g of sodium d-thionite are added at 60° C. and the mixture is stirred for 12 h at this temperature. The mixture is then cooled to 5° C. and carefully neutralized with 37% strength hydrochloric acid, the solution immediately turning cloudy. The mixture is stirred for 1 h at 0° C. Customary work-up gives 2.05 g of luteolin with a purity of 98.8%.

What is claimed is:

1. A process for preparing a compound of formula I

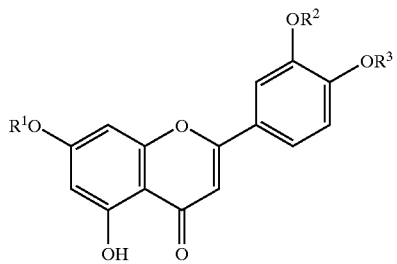

(I)

wherein
R$^1$ is H or (CH$_2$)$_m$OH,
R$^2$ is H or (CH$_2$)$_p$OH,
R$^3$ is H or (CH$_2$)$_p$OH, and
m, n and p are in each case, independently of one another, 2 to 8,
comprising reducing a compound of formula II

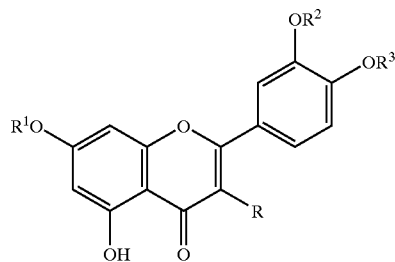

(II)

wherein R$^1$, R$^2$ and R$^3$ in each case, independently of one another, have the meanings given in formula I, and R is 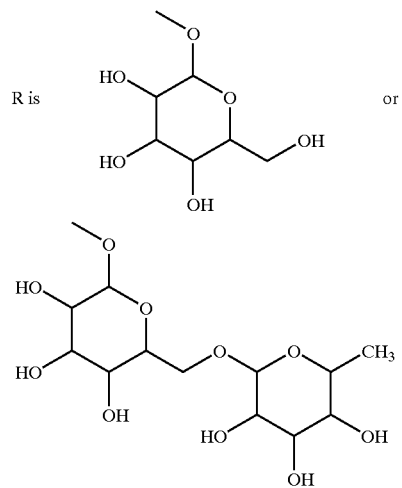

with sodium dithionite Na$_2$S$_2$O$_4$ in an aqueous alkaline medium.

2. A process as claimed in claim 1, wherein the compound of formula II is rutin, isoquercetin, a rutin derivative, an isoquercetin derivative or a mixture thereof.

3. A process as claimed in claim 1, wherein the compound of formula II is reduced at a temperature of 25 to 100° C.

4. A process as claimed in claim 1, wherein the compound of formula II is reduced at a pH of 7.5 to 11.

5. A process as claimed in claim 1, wherein the aqueous alkaline medium comprises an alkali metal hydroxide, an alkaline earth metal hydroxide, a hydrogencarbonate or a carbonate.

6. A compound of the formula I*

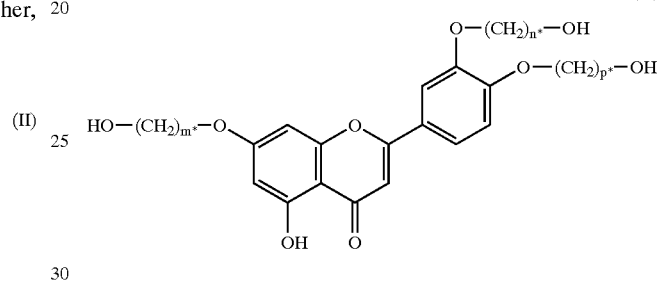

(I*)

in which m*, n* and p* in each case, independently of one another are 2 to 8.

7. A foodstuff comprising a compound of formula I from claim 1, wherein at least one of R$^1$, R$^2$ or R$^3$ is (CH$_2$)$_x$ OH, wherein x is 2 to 8.

8. A foodstuff comprising a compound of formula I from claim 1, wherein at least one of R$^1$, R$^2$ or R$^3$ is (CH$_2$)$_x$ OH, wherein x is 2 to 8.

9. A foodstuff comprising a compound of formula I* from claim 6.

10. A food supplement comprising a compound of formula I* from claim 6.

11. A cosmetic or pharmceutical composition comprising a compound of formula I* from claim 6.

12. A composition according to claim 11, further comprising a UV filter.

13. A method of protecting skin and hair against solar radiation or preventing inflammation or an allergic reaction of the skin comprising applying to the skin a composition according to claim 11.

14. A UV filter an antioxident or a free-radical scavenger comprising a compound of formula I* from claim 6.

* * * * *

UNITED STATES PATENT AND TRADEMARK OFFICE
CERTIFICATE OF CORRECTION

PATENT NO.   : 6,538,021 B1
DATED        : March 25, 2003
INVENTOR(S)  : Herwig Buchholz et al.

It is certified that error appears in the above-identified patent and that said Letters Patent is hereby corrected as shown below:

Column 11,
Line 18, reads "(CH2)pOH," should read -- (CH2)mOH, --

Column 12,
Line 40, reads "A foodstuff" should read -- A food supplement --
Line 48, reads "pharmceutical" should read -- pharmaceutical --
Line 57, reads "an antioxident" should read -- an antioxidant --

Signed and Sealed this

Eighteenth Day of May, 2004

JON W. DUDAS
*Acting Director of the United States Patent and Trademark Office*